United States Patent
Tessier et al.

(10) Patent No.: US 7,553,488 B2
(45) Date of Patent: Jun. 30, 2009

(54) ANTIBODIES AGAINST S100A8 AND S100A9 PROTEINS FOR MODULATING INFLAMMATORY REACTIONS

(75) Inventors: Philippe A. Tessier, Cap-Rouge (CA); Carle Ryckman, Duberger (CA); Karen Vandal, Lac St-Charles (CA); Pascal Rouleau, Lac St-Charles (CA)

(73) Assignee: Université Laval, Cité Universitaire, Québec (CA)

( * ) Notice: Subject to any disclaimer, the term of this patent is extended or adjusted under 35 U.S.C. 154(b) by 0 days.

(21) Appl. No.: 10/517,319

(22) PCT Filed: Jun. 20, 2003

(86) PCT No.: PCT/CA03/00939

§ 371 (c)(1),
(2), (4) Date: Jul. 15, 2005

(87) PCT Pub. No.: WO2004/004770

PCT Pub. Date: Jan. 15, 2004

(65) Prior Publication Data

US 2005/0288211 A1   Dec. 29, 2005

Related U.S. Application Data

(60) Provisional application No. 60/393,520, filed on Jul. 5, 2002.

(51) Int. Cl.
*A61K 39/395* (2006.01)
(52) U.S. Cl. ............. 424/145.1; 424/130.1; 424/141.1; 424/152.1
(58) Field of Classification Search ............... 435/69.1
See application file for complete search history.

(56) References Cited

U.S. PATENT DOCUMENTS

| | | | | |
|---|---|---|---|---|
| 5,248,825 | A * | 9/1993 | Dinerstein et al. | 564/305 |
| 5,731,166 | A * | 3/1998 | Geczy et al. | |
| 6,103,497 | A * | 8/2000 | Hillman et al. | 435/69.1 |
| 6,706,683 | B1 * | 3/2004 | Seto et al. | 514/2 |
| 2002/0192228 | A1 * | 12/2002 | Hanash | 424/185.1 |
| 2005/0118688 | A1 * | 6/2005 | Freeze et al. | 435/101 |
| 2006/0281674 | A1 | 12/2006 | Tessier et al. | |
| 2007/0231317 | A1 | 10/2007 | Tessier et al. | |

FOREIGN PATENT DOCUMENTS

| EP | 0263072 | | 4/1988 |
|---|---|---|---|
| WO | WO00/18970 | * | 4/2000 |

OTHER PUBLICATIONS

Rouleau, P., et al. 2003 Clinical Immunology 107: 46-54.*
Hessian, P.A., et al. 2001 Eur. J. Biochem. 268: 353-363.*
Donato, Rosario: "Functional roles of S100 proteins, calcium-binding proteins of the EF-hand type" Biochimica et Biophysica Acta 1450 (1999), pp. 191-231.
Ravasi, Timothy et al.: "Probing the S100 protein family through genomic and functional analysis" Genomics 84 (2004), pp. 10-22.
Mauro Perretti et al., Mobilizing Lipocortin 1 in adherent human leukocytes downregulates their transmigration, Nat Medicine, 1996, 2: 1259-1262.
Eue et al., Transendothelial migration of 27E10+ human monocytes, International Immunology, 2000, vol. 12: 1593-1604.
Harrison et al., Oxidation Regulates the Inflammatory Properties of the Murine S100 Protein S100A8, The Journal of Biological Chemistry, 1999, vol. 274: 8561-8569.
Newton et al., The Human S100 Protein MRP-14 Is a Novel Activator of the β2 Integrin Mac-1 on Neutrophils, The Journal of Immunology, 1998, 160: 1427-1435.
Dunn C J et al: "Increased expression of neutrophil MRP8 and MRP14 is associated with vascular adhesion molecule activation and differential leukocyte infiltratioin in delayed-type hypersensitivity suggesting a proinflammatory role for S100 calcium-binding proteins" Biosis, XP002242712 abstract.
Yen Tina et al: "Induction of the S100 chemotactic protein, CP-10, in murine microvascular endothelial cells by proinflammatory stimuli", Blood, W.B. Saunders, Philadelphia, VA, US, vol. 90, No. 12, Dec. 15, 1997, pp. 4812-4821.
Lagasse E et al: "Mouse MRP8 and MRP14, two intracellular calcium-binding proteins associated with the development of the myeloid lineage" Blood, W.B. Saunders, Philadelphia, VA, US, vol. 79, 1992, pp. 1907-1915.
Lackmann M.:"Identification of a chemotactic domain of the pro-inflammatory S100 Protein CP-10", Journal of Immunology, The Williams and Wilkins Co. Baltimore, US, vol. 150, No. 7, Apr. 1, 1993, pp. 2981-2991.
Devery, Jannine M et al: "Acute inflammatory activity of the S100 protein CP-10: Activation of neutrophils in vivo and in vitro." Journal of immunology, vol. 152, No. 4, 1994, pp. 1888-1897.
Ryckman Carle et al: "Proinflammatory activities of S100: Proteins S100A8, S100A9, and S100A8/A9 induce neutrophil chemotaxis and adhesion." Journal of Immunology, vol. 170, No. 6, Mar. 15, 2003, pp. 3233-3242.
Rouleau Pascal et al: The calcium-binding protein S100A12 induces neutrophil adhesion, migration, and release from bone marrow in mouse at concentrations similar to those found in human inflammatory arthritis., Clinical immunology (Orlando), vol. 107, No. 1, Apr. 20, 2003, pp. 46-54.
Geczy C., 1996, "Regulation and proinflammatory properties of the chemotactic protein, CP-10.", Biochimica et Biophysica Acta, 1313: 246-252.

(Continued)

*Primary Examiner*—Phillip Gambel
*Assistant Examiner*—Sharon Wen
(74) *Attorney, Agent, or Firm*—Ogilvy Renault, LLP

(57) ABSTRACT

The present invention relates to compounds and methods for modulating, reducing or inhibiting, inflammatory reactions in a patient. Particularly, inflammatory reactions that are targeted by the present invention are cell migration, secretion of toxic products and proteolysis at a site of inflammation. Reduction of inflammation manifestations and reactions occurs by using an anti-S100 polynucleotide or polypeptide inhibitor or antagonist, which is essentially targeted against S100A8, S100A9 or S100A12, alone or in combination with other inhibitors of chemokines or immune modulating products.

2 Claims, 12 Drawing Sheets

OTHER PUBLICATIONS

Odink K. et al., 1987, "Two calcium-binding proteins in infiltrate macrophages of rheumatoid arthritis.", Letters to Nature, vol. 330, pp. 80-82.

Ryckman C. et al., 2004, "Monosodium urate monohydrate crystals induce the release of the proinflammatory protein S100A8/A9 from neutrophils.", Journal of Leukocyte Biology, vol. 76, pp. 433-440.

Frosch M. et al., 2000, "Myeloid-related proteins 8 and 14 are specifically secreted during interaction of phagocytes and activated endothelium and are useful markers for monitoring disease activity in pauciarticular-onset juvenile rheumatoid arthritis.", Arthritis & Rheumatism, vol. 43, No. 3, pp. 628-637.

* cited by examiner

A

B

A

B

ANTIBODIES AGAINST S100A8 AND S100A9 PROTEINS FOR MODULATING INFLAMMATORY REACTIONS

CROSS-REFERENCE TO RELATED APPLICATIONS

This application is the national phase entry in the United States of PCT/CA2003/000939 filed on Jun. 20, 2003 and claims priority on U.S. provisional application Ser. No. 60/393,520 filed on Jul. 5, 2002.

TECHNICAL FIELD

The present invention relates to inhibitors, antagonists and methods for modulating the factors involved in body inflammation reactions and diseases. Particularly, the present invention relates to a method for reducing or inhibiting the symptoms and manifestations associated with body inflammations.

BACKGROUND ART

The acute articular inflammation of gouty arthritis is caused by crystallisation of sodium urate in an articulation. Interaction between monosodium urate crystals (MSU crystals) and monocytes, platelets, synoviocytes, macrophages and neutrophils within the articulation initiates an inflammatory response by stimulating the secretion of proinflammatory agents and chemotactic factors from these different cell types. Some of these mediators induce the accumulation of neutrophils, which further enhances the inflammatory response and release of oxygen radicals and proteolytic enzymes, leading to the destruction of the articulations.

Arthritis is a chronic syndrome characterized by the inflammation of peripheral joints, while gout manifests itself as an inflammation of the lower leg. Although the causal agents differ between the two diseases, the mechanism of migration of neutrophils is similar in both diseases. Therefore, for the sake of brevity, whenever reference hereinbelow is made to arthritis, it should be understood as encompassing gout, since both diseases are similar. There is a wide spectrum of disease severity and many patients run a course of intermittent relapses and remissions with an overall pattern of slowly progressive joint destruction and deformity. Persistent inflammation produces symptoms and damages tissue causing loss of cartilage, erosion of bone matter and subluxation of the joint. This results in a high degree of morbidity resulting in disturbed daily life of the patient. Diagnosis of arthritis is typically carried out by determination of rheumatoid factors in the blood and radiological changes in peripheral joints.

Transendothelial migration of neutrophils is a critical stage in the development of the inflammatory reaction. To infiltrate an articulation, the neutrophils must migrate from the blood through the endothelium and the synovial tissue. This migration occurs through a multistep process.

First, interactions between integrins, selectins and glycans mediate neutrophil rolling along the endothelium. Neutrophils are then activated, leading to changes in $\beta_2$ integrin to an active conformation. This change of conformation is thought to be induced by chemotactic factors expressed by endothelial cells such as platelet activating factor (PAF) or interleukin-8 (IL-8). Activation of integrins causes neutrophils to adhere strongly to the endothelium, allowing them to extravasate. Once in the tissue, neutrophils follow concentration gradients of chemoattractants such as complement peptide C5a, leukotriene $B_4$ ($LTB_4$) and IL-8.

Factors involved in neutrophil migration in gout pathogenesis remain largely unknown. For example, while $LTB_4$ is known to be produced by MSU crystal-activated neutrophils, inhibition of $LTB_4$ synthesis does not reduce MSU crystal-induced neutrophil recruitment in the subcutaneous air pouch model in rats. However, inhibition of PAF partially diminishes MSU crystal-induced arthritis in rabbits articulations. It has been observed that IL-8 can be the major cystein-x-cystein (C-X-C) chemokine involved in neutrophil migration in response to MSU crystals. Inactivation of IL-8 with specific blocking antibodies seems to lead to a reduction of neutrophil migration in rabbit articulations.

However, this reduction was observed 12 hours after MSU crystals injection, with no effect detected at earlier time points. This strongly suggests that IL-8 is not responsible for the initiation of the inflammatory response induced by MSU crystals. However, early neutrophil migration in response to MSU crystals is impaired in mice deficient in the murine IL-8 receptor homologue CXCR2. Since CXCR2 does not solely bind IL-8, this suggest that other chemokines or inflammatory mediators could be involved at the beginning or even during the inflammatory response.

Primary treatments of arthritis include first line drugs for control of pain and inflammation classified as non-steroidal anti-inflammatory drugs (NSAIDs), e.g., aspirin, ibuprofen, naproxen, methotrexate, etc. Secondary treatments include corticosteroids, slow acting antirheumatic drugs (SAARDs) or disease modifying drugs (DMs), e.g., penicillinamine, cyclophosphamide, gold salts, azothipprine, levamisole, etc.

All of the above-mentioned products have a variety of toxic side effects and most of them are cytotoxic. These drugs have limited advantages and their effects are mainly of short term duration. The side effects they produce, e.g., gastric erosion, and adverse effects on the kidneys and liver, dictate against their use over extended periods of time. Further the products primarily used are costly and have low benefit-risk ratios.

There still remains a need for alternative therapies, methods, and compositions or compounds for the modulation of inflammatory reactions which are moderate in cost, safe, efficient and which eliminate the need for traditional products and their associated side effects, particularly over prolonged daily use.

DISCLOSURE OF THE INVENTION

One object of the present invention is to provide a method for systemic modulation of an inflammatory reaction in an individual, a human or an animal in need, comprising administrating to the individual an effective amount of A chemotactic factor inhibitor, the chemotactic factor being selected from the group consisting of an S100 protein, a protein of the MRP family, calprotectin, and calgranulin.

The modulation can totally or partially inhibit the inflammatory reaction or totally or partially increase the inflammatory reaction.

The inflammatory reaction may be selected from the group consisting of arthritis, chronic polyarthritis, rheumatoid arthritis, gout, asthma, psoriasis, paraneoplastic syndrome, tumor-induced inflammatory diseases, turbid effusions, collagenosis, postinfectious arthritis, seronegative spondylarthritis, vasculitis, sarcoidosis, arthrosis, cell chemotaxis, cell migration, cell recruitement, proteolysis, oxidative burst, and radical oxydation.

The cell that can be chemoattracted by the compound and method of the present invention can be selected from the group consisting of a neutrophil, a monocyte, a platelet, a synoviocyte, a macrophage, a lymphocyte, a leukocyte, and a phagocytic cell.

According to one object of the present invention, the administration can be performed by intravenous, oral, intranasal, subcutaneous, topical, or intraperitoneal administration.

The method of the present invention is preferably performed on an animal that is a mammal.

According to another object of the invention, an effective amount can be an amount of S100 protein inhibitor effective to induce inhibition or activation of an inflammatory reaction.

An inhibitor used to performed the method according to the present invention can be an antibody or a fragment thereof binding to the S100 protein or to a receptor or a cofactor thereof.

The inhibitor can alternatively be a sens or an anti-sens mRNA, or an inhibitor of transcription or translation of the S100 protein factor, or an inhibitor of activity acquisition of the chemokine factor.

The inhibitor can also be a peptide binding to the S100 protein. Preferably, the S100 protein targeted in the present invention is an S100A8, S100A9, or an S100A12 protein.

Another object of the present invention is to provide a composition for modulating an inflammatory reaction comprising a therapeutically affective amount of a chemotactic factor inhibitor selected from the group consisting of an S100 protein, a protein of the MRP family, calprotectin, calgranulin, a pharmaceutically acceptable carrier.

In accordance with the present invention there is provided the use of a S100 protein inhibitor in the manufacture of a composition for modulating inflammatory reaction.

One object of the present invention is to provide a method using anti-S100 antibody or antagonists in the manufacture of pharmaceuticals to reduce the manifestations and reactions of inflammation in a patient in need by an administration of the pharmaceutical for a determined period of time.

Another object of the present invention is to provide a method in which anti-S100 antibody is targeted essentially against the S100A8 and S100A9 proteins.

A further object of the present invention is to provide a method, wherein an anti-S100 antibody can be used alone or in combination with one or more other antibodies, or in combination with any other immune modulating product. The expression "immune modulating product" is intended to mean any product, compound, or agent that has an inhibitory or stimulatory effect on at least one immunological reaction involved in any body inflammation.

Another object of the present invention is to provide a method, wherein the anti-S100 antibody is a polyclonal or a monoclonal antibody.

Also, one object of the present invention is to provide a method in which a composition comprising at least one antagonist or inhibitor as defined herein, can be in a form for subcutaneous, intravenous, intramuscular, intra-articular, oral, intranasal, or intraperitoneal administration.

Another object of the present invention is to provide a method that can be applied to humans as well as animals.

For the purpose of the present invention the following terms are defined below.

The term "gout" is intended to mean a metabolic disorder related to a blood excess of uric acid, characterized by a painful articular inflammation.

The terms "modulation" or "modulating" as used herein is intended to mean reducing or increasing a reaction, such as an inflammatory reaction. The modulation can be preferably a treatment. "Treatment" as used herein includes systemic use for the alleviation, amelioration or control of inflammation, e.g. of inflammatory rheumatic or rheumatoid disease, process, condition or event. It also includes intervention for the alleviation, amelioration or control of the sequelae or symptoms of inflammation, for example degeneration (e.g. of cells, epithelia or tissues), or especially swelling, exudation or effusion, or pain. In this context the term "treatment" is further to be understood as embracing use to reverse, restrict or control progression of any specified disease, process, condition, event or the like, including use for disease modifying effect. If any of the mentioned diseases, processes, conditions or events is associated with pain, the term "treatment" preferably encompasses the alleviation, amelioration or control (including temporal or permanent removal) of at least one further sequela or symptom in addition to pain, such as swelling, effusion, exsudation, stiffness, lack of flexibility of joints, or degeneration, more preferably of all symptoms and most preferably of the total clinical picture of the respective disease, irritation or manifestation.

MODES OF CARRYING OUT THE INVENTION

Figure 1:
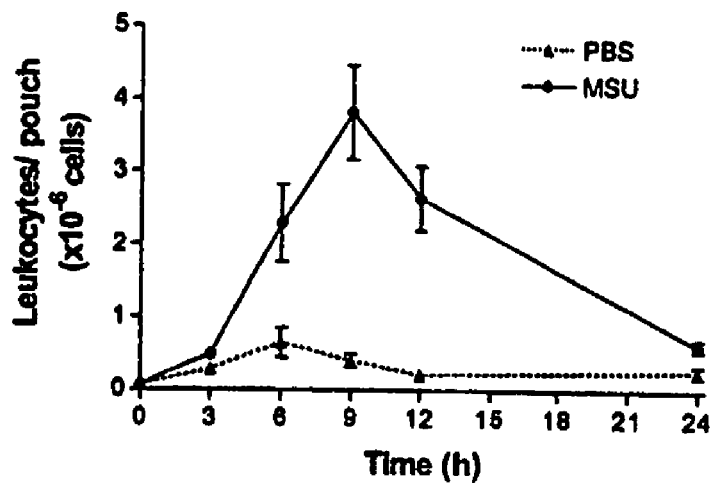
FIGS. 1A and 1B illustrate the MSU crystals-induced accumulation of leukocytes in the mouse air pouch model.
Figure 1:
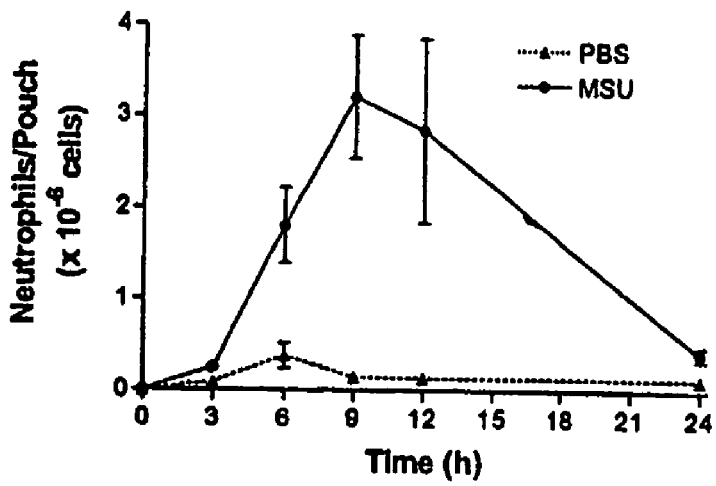

In accordance with the present invention, there is provided a method and compositions for the modulation of the activity of different factors involved in the manifestations or reactions oF body inflammation. The factors can cause migration of cells, such as for example but without limiting it to, neutrophils, or can cause oxidation by radicals, or proteolysis by different enzymes of proteases.

The present invention shows that myeloid-related proteins (MRP) play a role in the process of neutrophil migration to inflammatory site. MRP proteins are a subfamily of S100 proteins in which three members have been characterized, namely S100A8, S100A9, and S100A12. These small proteins are constitutively expressed at high levels in the cytosol of neutrophils. S100A8 and S100A9 are also expressed by activated endothelial cells, certain epithelial cells, keratinocytes, monocytes and activated macrophages. In the presence of calcium, S100A8 and S100A9 associate noncovalently to form the heterodimer S100A8/A9.

Several proinflammatory activities have been identified for these proteins. In vitro studies described herein below demonstrate that S100A8, S100A9, and S100A8/A9 are involved in neutrophil and monocyte migration and stimulate neutrophil adhesion to fibrinogen by activating the $\beta_2$ integrin Mac-1. In addition, intraperitoneal injection of murine S100A8 in mice stimulates the accumulation of activated neutrophils and macrophages. It is also shown that S100A9 and S100A8/A9 enhance monocyte adhesion to and migration through endothelial cells via Mac-1/ICAM-1 interactions.

S100A8 and S100A9 play a certain role in neutrophil migration as chemotractants. The extracellular presence of S100A8/A9 has been demonstrated in several pathologies including rheumatoid arthritis, tuberculosis and Crohn's disease. Local secretion of the proteins can be detected in periodontal infections and during experimental murine abscesses.

One particular embodiment of the present invention is to provide compounds and a method for neutralizing the chemotractant activity of the S100 proteins to reduce or inhibit cell migration at a site of inflammation.

Several observations demonstrate that S100A8 and S100A9 proteins play an essential role in the pathogenesis, for example but without limiting it to, of gout. In mice injected with MSU crystals, the proinflammatory proteins S100A8 and S100A9, which are present in air pouch exudates, were found to induce the migration of neutrophil to the air pouch with a kinetic similar to MSU crystals. In addition, inactivation of both S100A8 and S100A9 led to a total inhibition of neutrophil accumulation in response to MSU crystals, clearly demonstrating their involvement in neutrophil recruitment in vivo. High concentrations of these MRP proteins are found in the synovial fluids of gout patients.

In another embodiment of the present invention it is shown that S100A8 and S100A9 proteins are particular targets for the treatment of one of the most important symptoms in inflammatory patients, namely acute arthritic articular inflammation. This approach is now supported herein below with the inhibition of the S100A8, S100A9 and S100A8/A9 activity by using anti-S100A8 and anti-S100A9 antibodies.

Indeed, inactivation of S100A9 by passive immunization reduces neutrophil recruitment at a low level. However, inactivation of S100A8 reduces neutrophil recruitment by at least 50%. This data indicate that S100A8 plays a more important role in MSU crystals-induced neutrophil recruitment than S100A9. According to another embodiment of the present invention, passive immunization with anti-S100A8 and anti-S100A9 prior to injection of MSU crystals leads to a significant reduction or even total inhibition of neutrophil recruitment at the site of inflammation.

Alternatively, injection of antibodies specific to S100 proteins according to the present invention allows for the inactivation of the heterocomplex S100A8/A9, which is an important form found in the air pouch following MSU crystals injection. As S100A8/A9 is also a chemotactic factor for neutrophils and induces neutrophil accumulation in vivo, it will be recognized by someone skilled in the art that S100A8/A9 can also play a crucial role in MSU crystals-induced recruitment.

As anti-S100A8 and anti-S100A9 antibodies are effective to inactivate the S100A8, S100A9 and S100A8/A9 activity, and thus to prevent neutrophil recruitment, the use of these antibodies also represents an excellent way to prevent inflammatory symptoms and reactions, such as for example, but without limiting it to, acute arthritic articular inflammation.

In another embodiment of the present invention, there are provided antibody-based therapies that involve administering antibodies specific to S100 proteins to an animal, preferably a mammal, and most preferably a human patient for treating one or more of the disclosed diseases, disorders, or conditions. Therapeutic compounds of the invention include, but are not limited to, antibodies of the invention (including fragments, analogs and derivatives thereof), peptides binding to S100 proteins and nucleic acids encoding antibodies of the invention (including fragments, analogs and derivatives thereof and anti-idiotypic antibodies). The antibodies can be used to treat, inhibit or prevent diseases, disorders or conditions associated with aberrant expression and/or activity of a polypeptide of the invention, including, but not limited to, any one or more of the inflammatory diseases, disorders, or conditions described herein. The treatment and/or prevention of inflammatory diseases, disorders, or conditions associated with expression and/or activity of an S100 protein inhibitor or antagonist includes, but is not limited to, alleviating symptoms associated with those diseases, disorders or conditions. Anti-S100 antibodies can be provided in pharmaceutically acceptable compositions as known in the art or as described herein.

A summary of the ways in which the antibodies of the present invention may be used therapeutically includes binding S100 polynucleotides or polypeptides locally or systemically in the body or by direct cytotoxicity of the antibody, e.g. as mediated by complement (CDC) or by effector cells (ADCC). Some of these approaches are described in more detail below.

The antibodies of this invention may be advantageously utilized in combination with other monoclonal or chimeric antibodies, or with lymphokines. The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient, is preferred. Thus, in a preferred embodiment, human antibodies, fragments, derivatives, analogs, or nucleic acids, are administered to a human or animal patient for therapy or prophylaxis.

It is preferred to use high affinity and/or potent in vivo inhibiting and/or neutralizing antibodies against S100 polypeptides or polynucleotides of the present invention, fragments or regions thereof, for therapy of disorders related to S100 polynucleotides or polypeptides, including fragments thereof, of the present invention. Such antibodies, fragments, or regions, will preferably have an affinity for S100 polynucleotides or polypeptides of the invention, including fragments thereof.

Inhibition or reduction of the activity of S100 polynucleotides or polypeptides may be useful in treating diseases, disorders, and/or conditions of the immune system, by inhibiting the proliferation, differentiation, or mobilization (chemotaxis) of immune cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, inhibitors or antagonists of S100 polynucleotides or polypeptides can be used as a marker or detector of a particular immune system disease or disorder.

Similarly, allergic reactions and conditions, such as asthma (particularly allergic asthma) or other respiratory problems, may also be treated, prevented, and/or diagnosed by inhibitors of S100 polynucleotides or polypeptides, or antagonists of S100 polynucleotides or polypeptides. Moreover, these molecules can be used to treat anaphylaxis, hypersensitivity to an antigenic molecule, or blood group incompatibility.

S100 polynucleotides or polypeptides are chemotactic molecules that attract or mobilize cells (e.g., monocytes, fibroblasts, neutrophils, T-cells, mast cells, eosinophils, epithelial and/or endothelial cells) to a particular site in the body, such as an inflammation site, an infection site, or a site of hyperproliferation. The mobilized cells can then fight off and/or heal the particular trauma or abnormality.

Inhibitors or antagonists of S100 polynucleotides or polypeptides are provided to decrease chemotactic activity to any immunological cells. These inhibitors or antagonists of S100 chemotactic molecules can then be used to treat and/or prevent inflammation, infection, hyperproliferative diseases, disorders, and/or conditions, or any immune system disorder by decreasing the number of cells targeted to a particular location in the body. For example, inhibitors or antagonists of S100 chemotactic molecules can be used to treat and/or prevent wounds inflammation and other trauma to tissues by neutralizing the attraction of immune cells to the injured location Inhibition of S100 proteins can be achieved by using antibodies or inhibitors that bind or block access to the S100 proteins to a binding site or to any activation site activated by them.

The inhibitors or antagonists of S100 proteins can be employed to inhibit chemotaxis and activation of macrophages and their precursors, and of neutrophils, basophiles, B lymphocytes and some T cell subsets, e.g., activated and CD8+ cytotoxic T cells and natural killer cells, in auto-immune and chronic inflammatory and infective diseases. Examples of auto-immune diseases include rheumatoid arthritis, multiple sclerosis, and insulin-dependent diabetes. Some infectious diseases include silicosis, sarcoidosis, idiopathic pulmonary fibrosis caused by preventing the recruitment and activation of mononuclear phagocytes, idiopathic hyper-eosinophilic syndrome caused by preventing eosinophil production and migration, endotoxic shock caused by preventing the migration of macrophages and their production of the chemokine polypeptides of the present invention. The antagonists may also be used for treating atherosclerosis, by preventing monocyte infiltration in the artery wall.

The inhibitors or antagonists may also be used to treat histamine-mediated allergic reactions by inhibiting S100 protein-induced mast cell and basophil degranulation and release of histamine.

The inhibitors or antagonists may also be used to treat inflammation by preventing the attraction of monocytes to a wound area. They may also be used to regulate normal pulmonary macrophage populations, since acute and chronic inflammatory pulmonary diseases are associated with sequestration of mononuclear phagocytes in the lung.

The inhibitors or antagonists may also be used to treat rheumatoid arthritis by preventing the attraction of monocytes into synovial fluid in the joints of patients. Neutrophil and monocyte influx and activation play a significant role in the pathogenesis of both degenerative and inflammatory arthropathies.

The inhibitors or antagonists may be used to interfere with the deleterious cascades attributed primarily to IL-1 and TNF, which prevents the biosynthesis of other inflammatory cytokines. In this way, the antagonists may be used to prevent inflammation. The antagonists may also be used to inhibit prostaglandin-independent fever induced by S100 chemokines.

Alternatively, the inhibitors or antagonists of S100 proteins can be used in conjunction with IL-10, which is involved in the down regulation of neutrophil migration at an inflamed site, such as for example, but without limiting it to, Crohn's disease or ulcerative colitis.

The inhibitors or antagonists of S100 proteins can also be used to treat cases of bone marrow failure, for example, aplastic anemia and myelodysplastic syndrome. The inhibitors or antagonists may also be used to threat cases of leukemia such as, but not restricted to acute myeloid leukemia, chronic myeloid leukemia, and acute lymphoid leukemia. The inhibitors or antagonists can alternatively be used to treat or prevent graft rejection. The inhibitors or antagonists may also be used to treat asthma and allergy by preventing eosinophil accumulation in the lung. The antagonists may be employed in a composition with a pharmaceutically acceptable carrier, e.g., as hereinafter described.

The S100 chemokine polynucleotides or polypeptides inhibitors and antagonists of the present invention may be employed in combination with a suitable pharmaceutical carrier. Such compositions comprise a therapeutically effective amount of the polypeptide, and a pharmaceutically acceptable carrier or excipient. Such a carrier includes but is not limited to saline, buffered saline, dextrose, water, glycerol, ethanol, and combinations thereof. The formulation should suit the mode of administration.

The effects of S100 inhibitors or antagonists can be exploited in accordance with the present invention through recombinant DNA expression of these molecules, as well known in the art, of such inhibitors or antagonists in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, the cells can be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering an inhibitor or antagonist of the present invention should be apparent to those skilled in the art from the teachings of the present invention. For example, the expression vehicle for engineering cells may be other than a retrovirus, for example, an adenovirus which may be used to engineer cells in vivo after combination with a suitable delivery vehicle, or can be alternatively any desirable expression vector or plasmid.

The inhibitors or antagonists of the present invention are targeted against S100 polynucleotides or polypeptides, which include, but are not limited to, S100A8, S100A9, and S100A12, found as monomers, homodimers or heterodimers.

The inhibitors or antagonists can be an antibody used as a monoclonal antibody or a polyclonal antibody.

An antibody as defined herein, acting as inhibitor or antagonist of S100 protein, can be administered alone or in combination with other antibodies directed toward S100 polynucleotide or polypeptide.

The antibody is administered subcutaneously, intravenously, intramuscularly, intra-articular or intraperitoneally.

In one embodiment of the present invention, antibodies anti-S100 proteins can be generated in a patient by simple immunization as it is well known in the art. The immunization can be performed by administration to a patient an S100 polypeptide or an S100 encoding polynucleotide. The resulting immunization will allow to reduce or inhibit the chemotractant activity of the S100 proteins.

The present invention will be more readily understood by referring to the following examples which are given to illustrate the invention rather than to limit its scope.

EXAMPLE I

Role of S100A8 and S100A9 in Neutrophil Recruitment Induced by MSU Crystals

Material and Methods

Recombinant Proteins and Polyclonal Antibodies

Murine S100A8 expression vector was a generous gift from Prof. H. J. Schluesener, (University of Tüibingen, Germany). Murine S100A9 cDNA was synthesized by RT-PCR from neutrophil RNA isolated using Trizol™ reagent according to the manufacturer's instructions (GibcoBRL, USA). S100A9 cDNA was cloned into the pET28 expression vector (Novagen, Madison, Wis.) and transformed in *E. coli* HMS174. Recombinant protein expression was induced with 1 mM IPTG for 16 h at 16° C. After incubation, cultures were centrifuged at 5,000×g for 10 min. The pellet was resuspended in PBS/NaCl 0.5 M/imidazole 1 mM and lysed by sonication. Lysates were then centrifuged at 55,000×g for 25 min, supernatants collected and the recombinant His-tag S100A9 and S100A8 were purified using a nickel column. His-tag proteins bound to the column were cleaved from their His-tag by adding 10 U of biotinylated thrombin and incubated for 16 h at room temperature. Recombinant S100A8 and S100A9 were eluted with PBS. The digestion and elution process was repeated once to cleave the remaining undigested recombinant proteins and biotinylated thrombin was extracted from the eluates using streptavidin-agarose (Pierce, Rockford, Ill.). Contaminating LPS was removed on polymyxin B-agarose column (Pierce, Rockford, Ill.). LPS contamination was lower than 1 pg of LPS per µg of recombinant protein, as detected by the Limulus amoebocyte assay (Sigma, St-Louis, Mo.).

Polyclonal antisera against human and murine recombinant S100A8 and S100A9 were generated after repeated injections in New Zealand White rabbits or CD1 rats at 4 or 2 weeks intervals respectively. Antisera titers were determined using direct ELISA and immunoblot. IgG from antisera were purified by protein A affinity chromatography (PIERCE, Rockford, Ill.)

Air Pouch Experiments

Ten to twelve weeks old CD-1 or BALB/c mice were obtained from Charles River, St-Colomban, Canada. Air pouches were raised on the dorsum by s.c. injection of 3 ml of sterile air on days 0 and 3. On day 7, 1.5 mg of MSU crystals suspended in a volume of 1 ml of endotoxin-free PBS (Sigma, St-Louis, Mo.) was injected into the air pouches. Alternatively, 1 ml of murine S100A8 or S100A9 at concentrations ranging from 0.01 to 10 µg/ml was injected into the air pouches. At specific times, the mice were killed by asphyxiation using $CO_2$, the air pouches were washed once with 1 ml of PBS-5 mM EDTA, and then twice with 2 ml of PBS-5 mM EDTA, and the exudates were centrifuged at 500×g for 5 minutes at room temperature. Cells were counted with a hematocytometer following acetic blue staining. Characterization of leukocyte subpopulations was performed by Wright-Giemsa staining of cytospin™ (VWR, Missisauga, Canada). In separate experiments, mice were injected i.p. 16 hours prior to injection of MSU crystals in the air pouch with 2 mg of purified IgG from rabbit antisera against murine S100A8 and S100A9 to inhibit their activities.

ELISAs

The detection of human and murine S100A8, S100A9, and S100A8/A9 was performed by coating 96-well plates with (100 µl/well) of human S100A8/A9-specific mAb 5.5 (generous gift of Nancy Hogg, IORF, London, UK), purified rabbit IgG against mouse S100A8 or mouse S100A9 (for detection of murine S100A9 and S100A8/A9), diluted to a concentration of 1 µg/ml in 0.1 M carbonate buffer pH 9.6. After overnight incubation, the plates were washed with PBS/0.1% Tween-20™ and blocked with PBS/0.1% Tween-20™/2% BSA for 30 min at room temperature. The samples and standards (100 µl) were added and incubated for 1 hour at room temperature. After three washes with PBS/0.1% Tween-20™, the plates were incubated for 1 hour at room temperature with 100 µl/well of 1/10,000 dilutions of antisera against human S100A9 (for the detection of human S100A8/A9) or with purified rat IgG against murine S100A9 or murine S100A8 (for the detection of murine S100A9, S100A8 and S100A8/A9). The plates were then washed three times and incubated with 100 µl/well of peroxidase-conjugated donkey anti-rabbit (1/7,500) (Jackson ImmunoResearch, Missisauga, Canada) or peroxidase-conjugated Goat anti-rat (1/10,000) (Jackson ImmunoResearch, Mississauga, Canada) in PBS/0.1% Tween-20™/2% BSA for 1 hour at room temperature. After three washes, the presence of IgG was detected with 100 µl of TMB-S according to the manufacturer's instructions and the OD was read at 500 nm.

Results

The activating potential of MSU crystals was first assessed to induce an inflammatory reaction in the murine air pouch model. As shown in FIG. 1, MSU crystals stimulated an important inflammatory reaction when injected in the air pouch. Leukocyte recruitment was first detected 3 hours after injection and reached maximum levels within 9 hours, before returning to control levels by 24 hours post-injection. More than 90% of the recruited leukocytes were neutrophils, the rest being monocytes.

Release of MRPs in the Air Pouch in Response to MSU Crystals Injection

Figure 2:
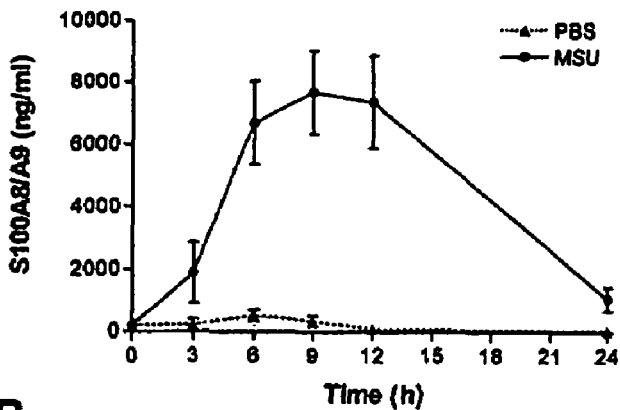
FIGS. 2A to 2C illustrate the release of S100A8, S100A9, and S100A8/A9 in air pouches of mice injected with MSU crystals.
Figure 2:
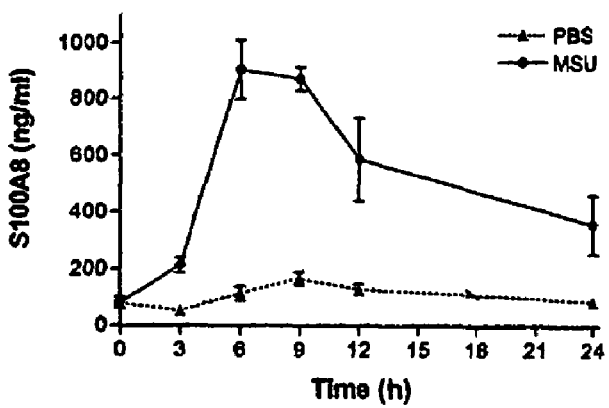
Figure 2:
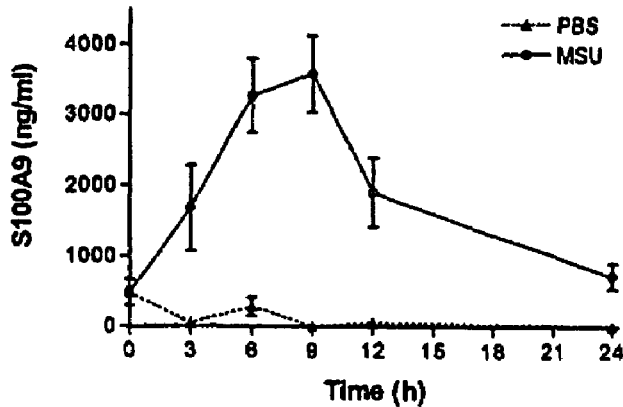

Knowing that high levels of MRPs are present in several inflammatory processes, we therefore quantified the presence of MRPs in the air pouch exudates following MSU crystals injection. Low levels of S100A8, S100A9, and S100A8/A9 were detected in air pouch exudates of non-injected mice. Injection of MSU crystals led to the release of 7.5 µg/ml of S100A8/A9, which is approximately 1000 times more than chemokines. This release was detected as early as 3 hours post-injection and was maximal between 6 to 12 hours following injection of MSU crystals. S100A8 and S100A9 homodimers were also present but at inferior concentrations (FIGS. 2A, 2B and 2C). The presence of MRPs in the pouch also correlated with neutrophil recruitment. These results suggested that MRPs could play a role in neutrophil recruitment in response to MSU crystals.

Role of S100A8 and S100A9 in Neutrophil Recruitment Induced by MSU Crystals

Figure 3:
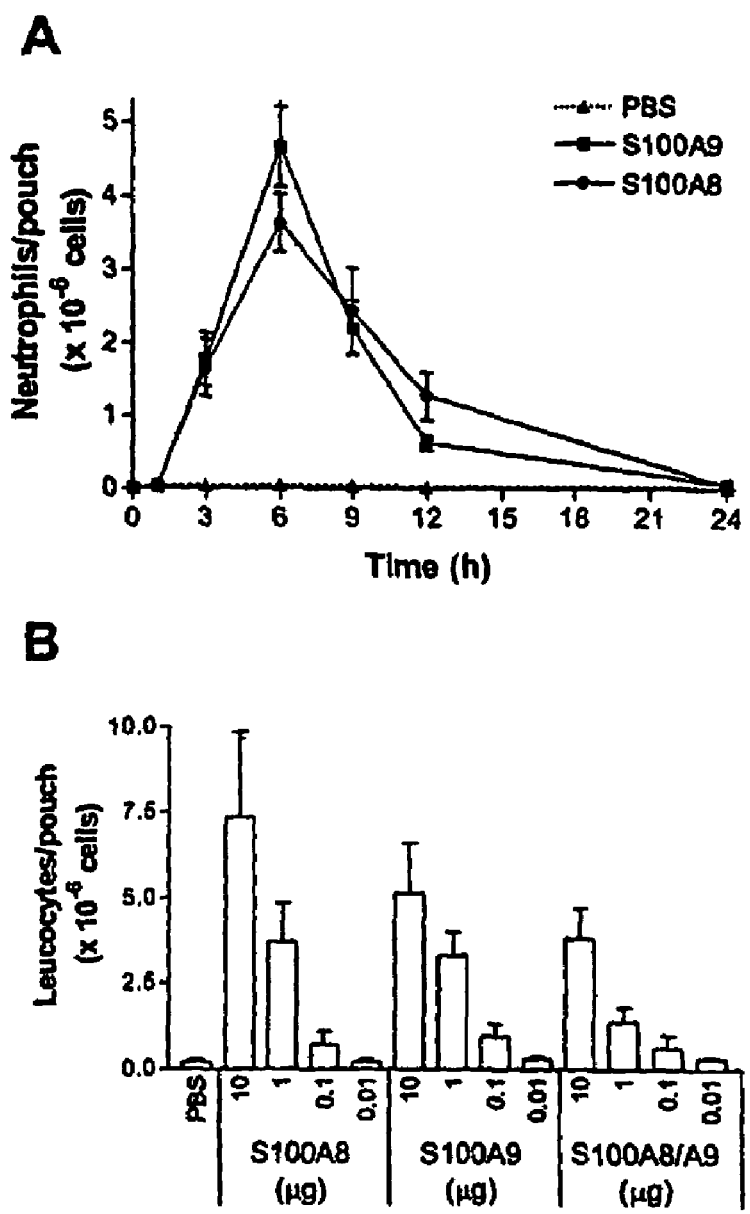
FIGS. 3A and 3B illustrate that S100A8, S100A9, and S100A8/A9 stimulate neutrophil accumulation in vivo.

To determine the role of MRPs in MSU-induced leukocyte recruitment, 10 µg of recombinant murine S100A8 and S100A9 were first injected in the air pouch to determine their proinflammatory activities in vivo. Injection of both murine S100A8 and S100A9 led to the accumulation of neutrophils in the air pouch. (FIG. 3A). Neutrophils recruitment occurred within 3 hours post-injection and was maximal between 6 and 9 hours post-injection, after which time it returned to control levels within 24 hours (FIG. 3A). More than 95% of the migrated leukocytes were neutrophils, with 5% of monocytes migrating as well. As shown in FIG. 3B, S100A8, S100A9, and also S100A8/A9 induced leukocyte recruitment to the air pouch in a dose-dependent fashion manner. Neutrophil recruitment occurred at injected doses as low as 0.1 µg, and was maximal at 10 µg. Those doses are similar to the levels detected in the air pouches following injection of MSU crystals (FIGS. 2A, B, and C).

Figure 4:
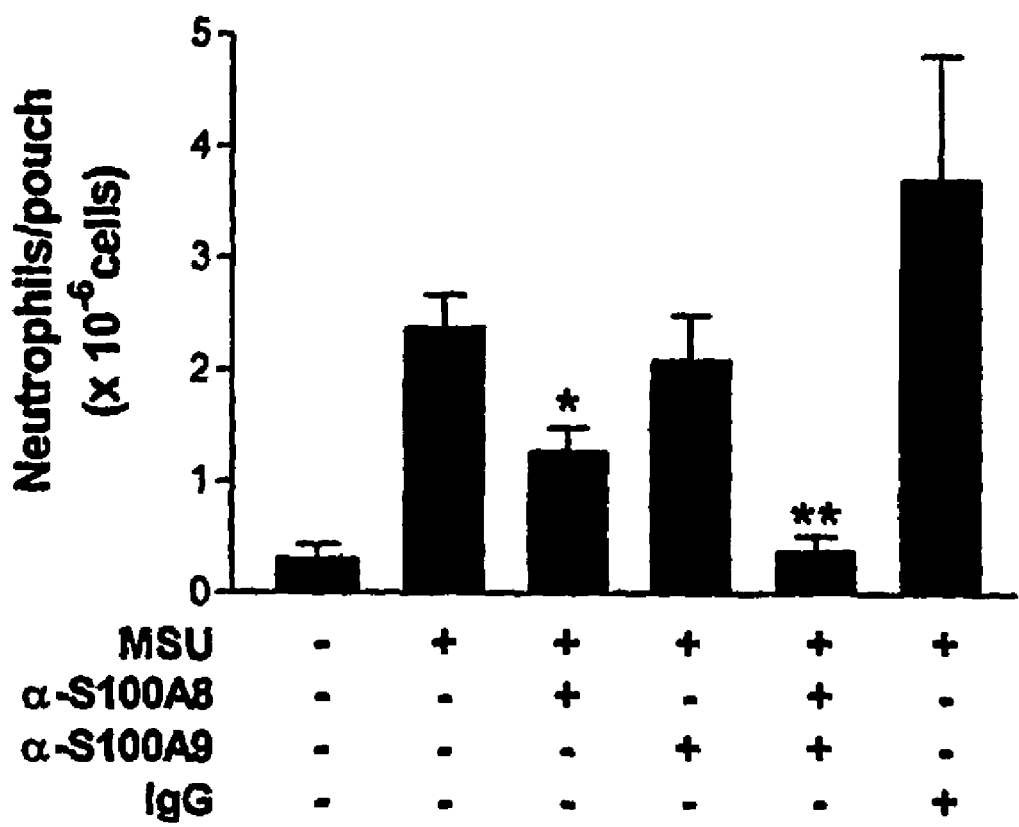
FIG. 4 illustrates that S100A8 and S100A9 are essentials to neutrophil accumulation induced by MSU crystals.

The role of S100A8 and S100A9 in neutrophil migration induced by MSU crystals was next investigated by inhibiting their activities using purified IgG from immunized rabbits. In preliminary experiments, anti-S100A8 and anti-S100A9 IgG specifically inhibited the recruitment induced in the air pouch following the injection of S100A8 and S100A9 respectively. Peritoneal injection of purified IgG from pre-immunized rabbits prior to MSU crystals injection in the air pouch slightly reduces neutrophil recruitment (FIG. 4). Injection of anti-S100A8 alone reduced neutrophil recruitment by more than 50% ($p<0.05$, Dunnett multiple comparison test). Moreover, injection of both anti-S100A8 and anti-S100A9 completely inhibited the neutrophil recruitment induced by MSU crystals to the air pouch ($p<0.01$). Since these antibodies bind to both homodimers and S100A8/A9 heterodimers, injection of both antibodies could have inactivated not only S100A8 and S100A9, but also S100A8/A9 activity.

Figure 5:
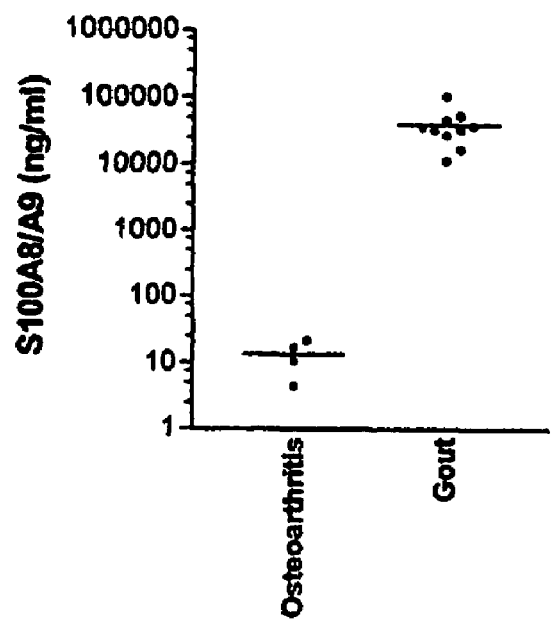
FIGS. 5A and 5B illustrate the measurement of S100A8/A9 in synovial fluids and plasma of patients with gout. S100A8/A9 was measured by ELISA in (A) plasma and (B) synovial fluids of healthy donors and patients suffering from gout, or osteoarthritis.
Figure 5:
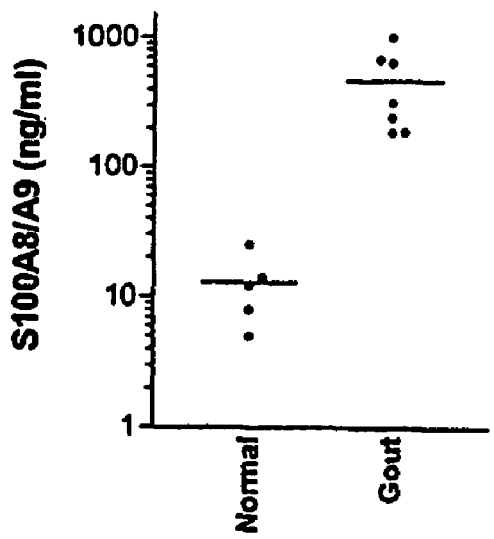

S100A8/A9 is Present in Synovial Fluids and Plasma of Patients Suffering from Gout Inhibition by anti-S100A8 and anti-S100A9 indicated that S100A8 and S100A9 were essential for neutrophil recruitment in MSU crystals-induced inflammatory reaction in vivo. To verify whether they could play a role in gout pathogenesis, we quantified S100A8/A9 by specific ELISA in synovial fluids and serum of several gout patients. S100A8/A9 was almost absent from synovial fluids of osteoarthritis patients, a disease with no synovial inflammation (FIG. 5A). In contrast, up to 100 µg/ml were measured in synovial fluids of gout patients. S100A8/A9 was also detected in the serum of the same patients where it reached 1 µg/ml, a concentration 100 times higher than measured in healthy donors (FIG. 5B). These concentrations, which are higher than the ones detected in the murine air pouch following MSU crystal injection, are consistent with a role for S100A8 and S100A9 in gout pathogenesis.

Conclusion

The proinflammatory proteins S100A8 and S100A9 which are also present in the air pouch exudates were found to induce neutrophil migration to the air pouch with a kinetic similar to MSU crystals. In addition, inactivation of both S100A8 and S100A9 led to a total inhibition of neutrophil accumulation in response to MSU crystals, clearly demonstrating their involvement in neutrophil recruitment in vivo. Since these proteins are also present at high concentrations in synovial fluids of gout patients, it is clear that they play an essential role in gout pathogenesis.

S100A8, S100A9, and S100A8/A9 were detected at high concentrations in the exudates of mice injected with MSU crystals and in the synovial fluid of patients suffering from gout. The release was rapid, reaching $10^{-8}$ M before 3 hours and close to $10^{-6}$ M within 6 hours post-injection. It was demonstrated that S100A8 and S100A9 are chemotactic at concentrations of $10^{-10}$ to $10^{-8}$ M and stimulate neutrophil adhesion at $10^{-7}$ to $10^{-6}$ M. This illustrates that they can direct neutrophil chemotaxis at early time points, before inducing their retention at the inflammatory site by stimulating their adhesion at later time. S100A8 and S100A9 release also correlated with neutrophil recruitment in the air pouch exudate. Release of MRPs by neutrophils, and monocytes has been demonstrated. The correlation between the release of MRPs and neutrophil recruitment, and the fact that 30% of the neutrophil cytosolic proteins are MRPs, shows that neutrophils are the primary source of MRPs in the air pouch following MSU crystals injection.

Neutralization of S100A9 by passive immunization can reduce the neutrophil recruitment. Inactivation of S100A8 reduced neutrophil recruitment by at least 50%. Passive immunization with anti-S100A8 and anti-S100A9 prior to injection of MSU crystals led to a total inhibition of neutrophil recruitment to the air pouch suggesting that both S100A8 and S100A9 play essential roles in the recruitment of neutrophils. Alternatively, injection of both antibodies could also inactivate the heterocomplex S100A8/A9, which is the major form found in the air pouch following MSU crystals injection. As S100A8/A9 is also chemotactic for neutrophils and induces neutrophil accumulation in vivo, these results support that S100A8/A9 can be exploited to play a role in MSU crystals-induced recruitment.

It was also demonstrated that human S100A8, S100A9 and S100A8/A9 are chemotactic for neutrophil at concentration of $10^{-10}$ M in vitro. S100A9 and S100A8/A9 are also shown to enhance monocyte adhesion and migration across endothelial cells via Mac-1/ICAM-1 interaction. Evidences were presented here for the first time that S100A8 and S100A9 play a chemotactic role in neutrophil migration in a mammal. The extracellular presence of S100A8/A9 can therefore be associated to several pathologies including rheumatoid arthritis, tuberculosis, ulcerative colitis, and Crohn's disease. This demonstrates that S100A8 and S100A9 play a role in other pathologies as well. This is also supported by the fact that S100A12 (the third member of the MRP subfamily of S100 proteins) is involved in inflammation associated with experimentally-induced colitis and delayed-type hypersensitivity.

The present invention also contemplates a variety of useful compositions. For example, a preferred composition capable of inhibiting inflammation in animals comprises different S100 protein inhibitors, wherein said inhibitors are capable of inhibiting different inflammatory reactions, as for example without limiting to, neutrophil migration, or superoxide production in phagocytic cells, in a pharmaceutically acceptable carrier or excipient. In a preferred embodiment, the animal is a human. Alternatively, preferred compositions according to the present invention may include any of the S100 protein inhibitor described hereinabove, for example, and without limitation, antibody, anti-sens mRNA, and antibody anti-chemokine factor receptor, to name but a few.

Another aspect of the invention relates to a method for directly inhibiting activation of the specific inflammatory reaction by phagocytic cells, and more preferably, human phagocytic cells. A further aspect relates to methods for preventing or decreasing the tissue damage associated with inflammatory reaction which involves administration of therapeutically effective amount of S100 protein inhibitor as described herein. The invention relates specifically to a method of preventing or decreasing symptoms such as gout, autoimmune disorders, myocardial infarction, adult respiratory distress syndrome (ARDS), asthma, and various dermatological disorders, which comprises the administration of an effective amount of a S100 protein inhibitor or a derivative to a patient in need of such treatment.

The present invention also contemplates medicaments, and methods of making same, many of which methods are well known in pharmaceutical practice. For example, the S100 protein inhibitors and derivatives of the present invention can be formulated into various forms for administration to mucous membranes, into intra-articular areas, intraperitoneally, intravascularly, topically, subcutaneously, and via suppository. Such medicaments may be formulated together with suitable carriers, excipients, binders, fillers, and the like into dosage forms, with each form comprising a fraction or a multiple of the daily dose required in order to achieve the desired treatment result.

It will also be appreciated that various combinations of the preceding elements may be made to provide other efficacious peptides, compositions, and methods according to the present invention.

EXAMPLE II

Blockade of S100 Proteins Suppresses Neutrophil Micgation in Response to LPS

Material and Methods

Recombinant Proteins

Murine S100A8 cDNA cloned into the pET28a expression vector (Novagen, Madison, Wis.) was a generous gift from Professor Hermann J. Schlüesener, U. of Tübingen, Germany. Murine S100A9 cDNA was obtained by RT-PCR and cloned in our laboratory into the same vector. Recombinant proteins were produced as previously described (Ryckman et al., 2003, J. Immunol. 160: 1427). Contamination by endotoxins was lower than 1 pg/µg of recombinant proteins as assessed using the Limulus amoebocyte assay. Recombinant S100A8/A9 was produced by mixing together equimolar quantities of recombinant S100A8 and S100A9 in the presence of HBSS supplemented with 10 mM HEPES, pH 7.4 containing 1.3 mM $Ca^{2+}$.

Production of Polyclonal Antibodies

New Zealand White rabbits (<2.5 kg) were immunized by intradermal dorsal injections (4 sites) with a total of 100 µg of purified murine recombinant S100A8 or S100A9 in 500 µl endotoxin-free PBS (Sigma, St-Louis, USA) mixed with an equal volume of Freund's complete adjuvant. Antibody responses were enhanced by repeated injections 3 and 6 weeks after the initial injection using the Freund's incomplete adjuvant. Antisera were collected and tested for specificity by ELISA and Western blots against purified recombinant S100A8 and S100A9. Immunoglobulin G (IgG) from antisera was purified by protein A affinity chromatography (PIERCE, Rockford, Ill.). The anti-S100A8 antiserum had titers of 1:100,000 and 1:500 for the detection in ELISA of 100 ng of S100A8 and S100A9 respectively. The anti-S100A9 antiserum had titers of 1:250 and 1:100,000 for the detection in ELISA of 100 ng of S100A8 and S100A9 respectively. Absence of cross reactivity of the purified IgG with the other murine myeloid related protein or proteins within the air pouch exudates was confirmed by immunoprecipitation assays and western blots.

CD Rats were immunized by i.p. injections with a total of 60 µg of purified murine recombinant S100A8 or S100A9 in 250 µl endotoxin-free PBS (Sigma, St-Louis, USA) mixed with an equal volume of Freund's complete adjuvant. Antibody response was enhanced by repeated injections 14, 28, and 42 days after the initial injection using the Freund's incomplete adjuvant. Antisera were collected and tested for specificity by ELISA and immunoblots against purified recombinant S100A8 and S100A9. The anti-S100A8 antiserum had titers of 1:10,000 and 1:500 for the detection of 100 ng of S100A8 and S100A9 respectively. The anti-S100A9 had titers of 1:250 and 1:10,000 for the detection of 100 ng of S100A8 and S100A9 respectively.

ELISA

For S100A8 and S100A9, Costar High Binding 96-well plates (Corning, N.Y., USA) were coated overnight at 4° C. with 100 µl/well of purified rabbit IgG against S100A8 or S100A9 diluted to a concentration of 1 µg/ml in 0.1 M carbonate buffer pH 9.6. The wells were blocked with PBS/0.1% Tween-20™/2% BSA (150 µl/well) for 30 min at room temperature. The samples and standards (100 µl) were added and incubated for 45 min at room temperature. The plates were washed 3 times with PBS/0.1% Tween-20™, and were incubated with rat IgG (100 µl/well) against S100A8 or S100A9 diluted in PBS/0.1% Tween-20™/2% BSA (1:10000) for 45 min at room temperature. The plates were then washed 3 times in PBS/0.1% Tween-20™. To reveal the immune complex, peroxidase-conjugated goat anti-rat IgG (H+L) (minimum cross-reaction to rabbit serum proteins) (100 µl/well) at a dilution of 1:10000 was added and incubated 45 min at room temperature. The plates were washed 3 times and 100 µl/well of TMB-S substrate were added according to the manufacturer's instructions. The optical densities (ODs) were read at 500 nm. The lower limit of quantification was determined as 4 ng/ml for both S100A8 and S100A9.

For S100A8/A9, 96-well plates were coated overnight at 4° C. with purified anti-S100A9 rabbit IgG (µl/100 well) diluted 1 µg/ml in 0.1 M carbonate buffer pH 9.6. The wells were blocked with PBS/0.1% Tween-20™/2% BSA (150 µl/well) for 30 min at room temperature. The samples and standards (100 µl) were added and incubated for 45 min at room temperature. The plates were washed 3 times with PBS/0.1% Tween-20™ then incubated with 100 µl/well anti-S100A8 rat IgG diluted in PBS/0.1% Tween-20™/2% BSA (1:10000) for 45 min at room temperature. The plates were next washed 3 times in PBS/0.1% Tween-20™ and incubated with 100 µl/well of peroxidase-conjugated goat anti-rat IgG at a dilution of 1:10000 for 45 min at room temperature. After 3 washes, 100 µl/well of TMB-S substrate were added according to the manufacturer's instructions. The ODs were read on a plate reader at 500 nm. The lower limit of quantification of this assay was determined as 10 ng/ml. All 3 ELISAs were tested using excess amounts (100 times) of S100A8, S100A9, or S100A8/A9 proteins and were shown to be specific under the conditions reported here.

Air Pouch Experiments

The experimental protocols were approved by the Laval University animal protection committee. Air pouches were raised on the dorsum of 10 to 12 weeks-old CD-1 mice (Charles River, St-Colomban, Canada) by s.c. injection of 3 ml of sterile air on days 0 and 3 (Tessier et al., 1997 J. Immunol. 159:3595). On day 7, 1 ml of LPS (1 µg/ml) or its diluent (PBS) was injected into the air pouches. At specific times, the mice were killed by asphyxiation using $CO_2$; peripheral blood was collected by cardiac puncture and diluted 1:20 in PBS-EDTA 5 mM. Total leukocytes were stained with acetic blue and counted using a hematocytometer. The air pouches were washed once with 1 ml PBS-5 mM EDTA, and then twice with 2 ml of PBS-5 mM EDTA, and the exudates were centrifuged at 500×g for 5 min at room temperature. Cells were counted with a hematocytometer following acetic blue staining. Characterization of leukocyte subpopulations in the blood and migrating into the pouch space was performed by Wright-Giemsa staining of cytospins. In some experiments, mice were injected i.p. with 2 mg of purified rabbit IgG from preimmune serum, anti-S100A8, or anti-S100A9 16 h before LPS injection in the air pouch.

Intravenous Injections

Animals were put on a heated cushion to dilate the tail vein 15 min before injection. Two hundred µl of S100A8, S100A9, or S100A8/A9 (0.006-60 µg/ml) was then injected i.v. in the tail vein of the mouse, corresponding to 0.05 to 500 µg of protein per kg of body weight. Animals were sacrificed by $CO_2$ asphyxiation at times ranging from 5 min to 24 h later; peripheral blood was collected by cardiac puncture and diluted 1:20 in PBS-EDTA 5 mM. Total leukocytes were counted using a hematocytometer following acetic blue staining. Bone marrow cells were collected by flushing with PBS-EDTA 5 mM through incisions made in the femur, followed by disaggregation. Cytospin preparations of both blood and bone marrow cells were analyzed after Wright-Giemsa differential staining.

Statistical Analyses

All statistical analyses were performed using the GraphPad Instate™ software (GraphPad Software Inc., San Diego, Calif.). Statistical comparisons were made by analysis of variance (ANOVA) for the number of leukocytes in air pouches, blood and bone marrow. The Bonferroni and Dunnett multiple comparison tests were used to compare specific groups at a confidence interval of 95%.

Results

Figure 6:
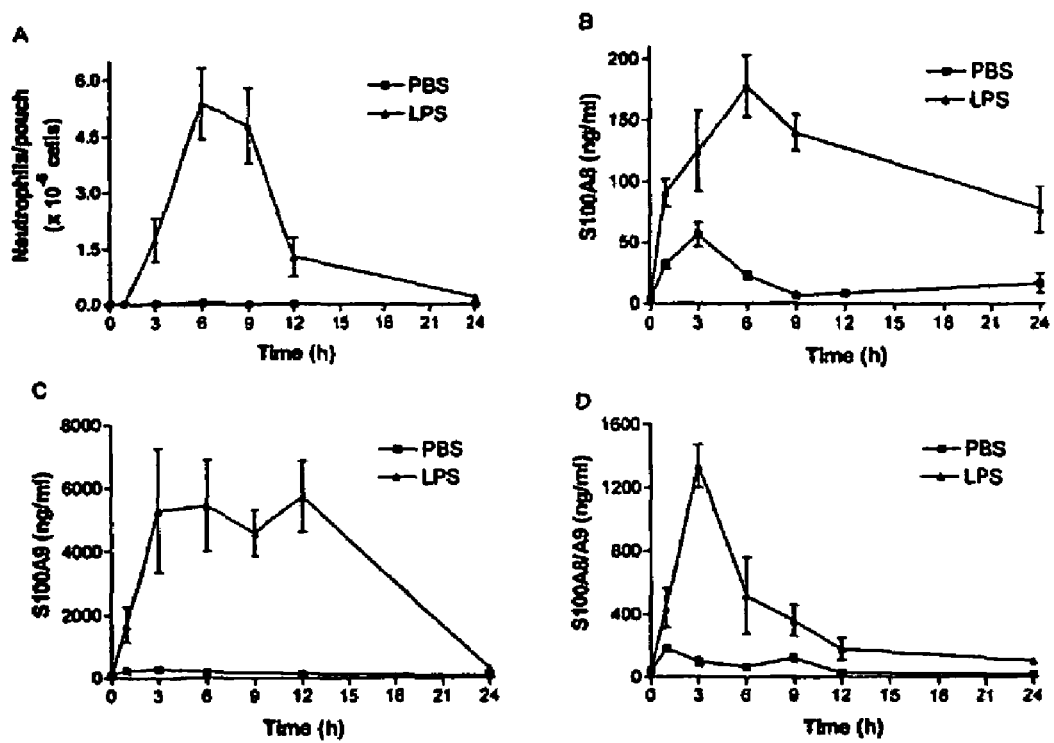
FIGS. 6A to 6D illustrate the neutrophil accumulation and secretion of S100A8, S100A9, and S100A8/A9 in the air pouch exudates following injection of LPS.

Release of S100A8, S100A9, and S100A8/A9 in the Extracellular Milieu Following Injection of LPS To examine the involvement of S100A8, S100A9, and S100A8/A9 in neutrophil migration, we first studied their release in vivo in response to LPS. The air pouch model was selected since this closed environment allows a clear measurement of immigrated leukocytes and released pro-inflammatory factors in the exudates. Few leukocytes were present in the pouch exudates prior to the injection of either PBS or LPS. Injection of PBS in the air pouch led to a very mild accumulation of neutrophils, probably consecutive to the injury caused by the needle. In contrast, injection of LPS led to an inflammatory reaction associated with redness of the air pouch and the presence of plasma proteins in the air pouch exudates. Injection of LPS also induced the rapid migration of leukocytes to the pouch, first detected 3 h post-injection (FIG. 6A). This accumulation was maximal at 6 h post-injection and almost returned to control levels by 12 h. More than 90% of the migrating leukocytes were neutrophils, with few monocytes migrating as well.

This accumulation was associated with the release of S100A8, S100A9, and S100A8/A9 in the pouch exudates. Low levels of S100A8, S100A9, and S100A8/A9 were detected in the exudates of non-injected or PBS-injected mice (FIGS. 6B-D). In contrast, injection of LPS led to the rapid release of all three S100 proteins. S100A8 was detected as early as 1 h post-injection of LPS (before neutrophil migration, FIG. 6A) and remained significantly above the control levels for the next 23 h. Similarly, the presence of S100A9 was maximal between 3 and 12 h post-injection of LPS, but the levels returned to control values by 24 h post-injection. In contrast, the presence of S100A8/A9 was more transitory, being maximal at 6 h post-injection of LPS and returning to control levels by 9 h post-injection. While S100A9 and S100A8/A9 concentrations were similar (3-5 µg/ml), S100A8 concentration was lower, reaching only 180 ng/ml. These results suggest that S100A8, S100A9, and S100A8/A9 are released separately during an inflammatory episode and precede neutrophil immigration.

S100A8 and S100A9 are Involved in Neutrophil Accumulation in Response to LPS

Figure 7:
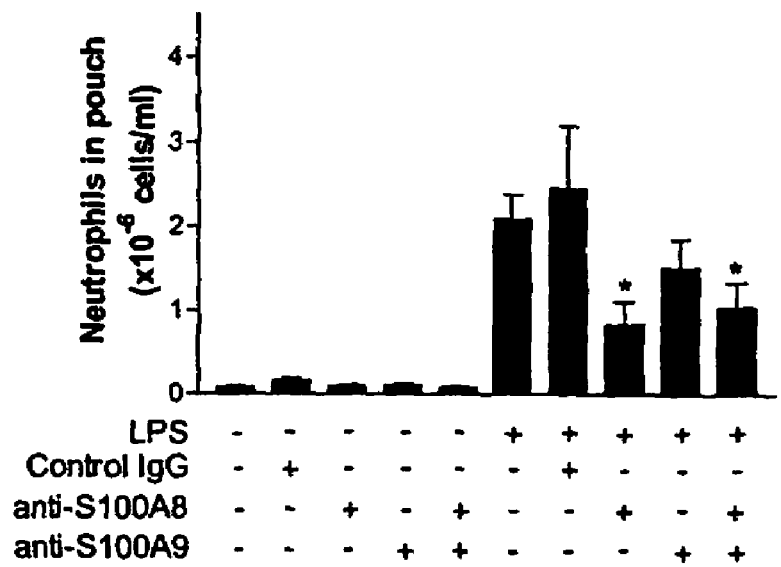
FIGS. 7A and 7B illustrate the effect of polyclonal antibodies against S100A8 and S100A9 on neutrophil accumulation induced by LPS.
Figure 7:
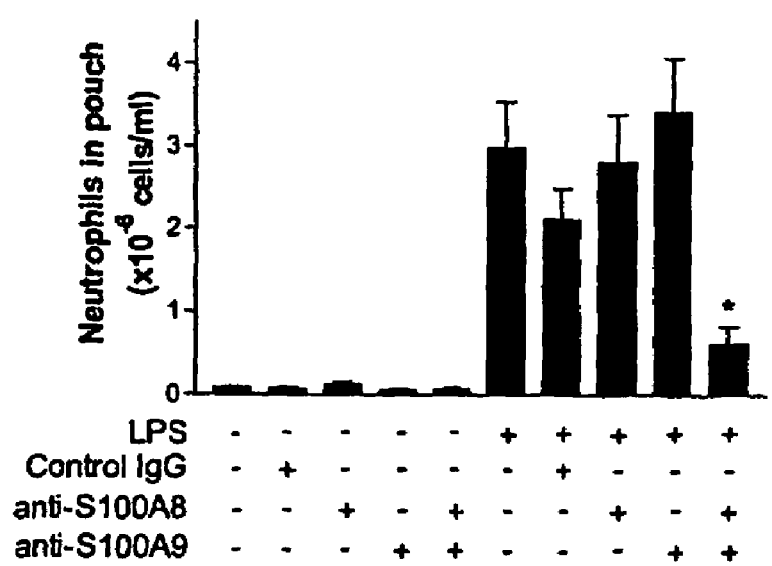

To evaluate the role played by S100A8 and S100A9 in neutrophil migration, mice were injected i.p. with purified rabbit IgG against S100A8 and S100A9. LPS was then injected in the air pouches and neutrophil accumulation was measured 3 and 6 h later. Anti-S100A8 and anti-S100A9 had no effect on neutrophil accumulation in PBS-injected mice (FIGS. 7A and B). Anti-S100A9 slightly reduced neutrophil accumulation 3 h following injection of LPS, but this reduction was not significant (FIG. 7A). In contrast, anti-S100A8 reduced LPS-induced neutrophil accumulation by 52% at 3 h post-injection (p<0.05, Bonferroni test). This inhibition was not enhanced by the addition of anti-S100A9. By 6 h post-injection, only the combination of anti-S100A8 and anti-S100A9 proved effective in preventing the migration of neutrophils to the air pouch in response to LPS (FIG. 7B, p<0.05, Bonferroni test). These antibodies inhibited neutrophil migration by 82%.

Presence of S100A9 and S100A8/A9 in the Serum Following Injection of LPS in the Air Pouch LPS induced the accumulation of more than $5.4 \times 10^6$ cells in the air pouches (FIG. 6A), twice the estimated number of neutrophil content of the blood (approximately $3 \times 10^6$ cells). LPS therefore stimulated the migration of neutrophils to the air pouch in numbers greater than were present in the blood.

Figure 8:
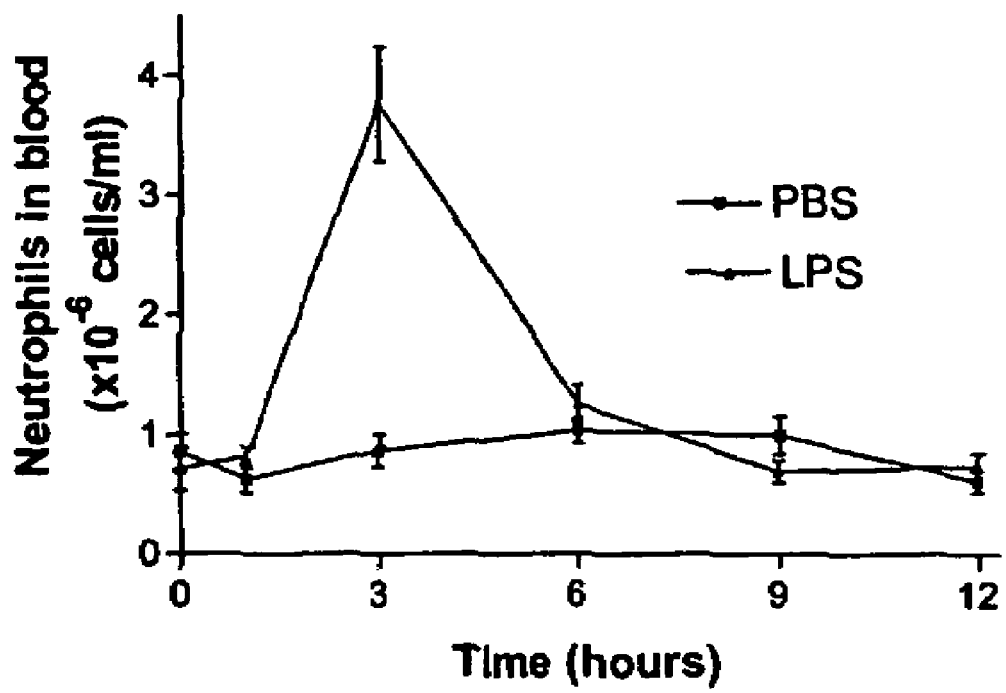
FIG. 8 illustrates the local LPS injection inducing neutrophilia in mice.
Figure 9:
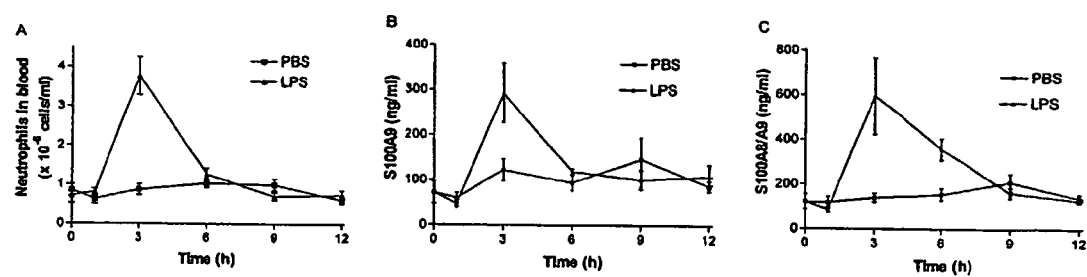
FIGS. 9A to 9C illustrate the presence of S100A9 and S100A8/A9 in the serum of mice injected with LPS.

This suggest that in mice LPS can either directly or indirectly induce neutrophilia. To confirm this, LPS was injected in the air pouches of mice and the number of neutrophils was evaluated in the blood. Injection of LPS in the air pouch led to a 4.3 fold increase in the number of neutrophils circulating in the blood 3 h after injection (FIG. 8). This augmentation was transient, returning to control levels at 6 h post-injection. The LPS-induced neutrophilia was associated with an increase in S100A9 and S100A8/A9 serum levels (FIGS. 9A and B). Similarly to the number of circulating neutrophils, this increase was maximal at 3 h post-injection and almost returned to control levels by 6 h post-injection, reaching a value of 292.9±66.0 ng/ml of S100A9 and 595.3±172.0 ng/ml of S100A8/A9 3 h post-injection. Contrarily to S100A9 and S100A8/A9 levels, the concentrations of S100A8 remained stable following injection of LPS in the air pouch.

Figure 10:
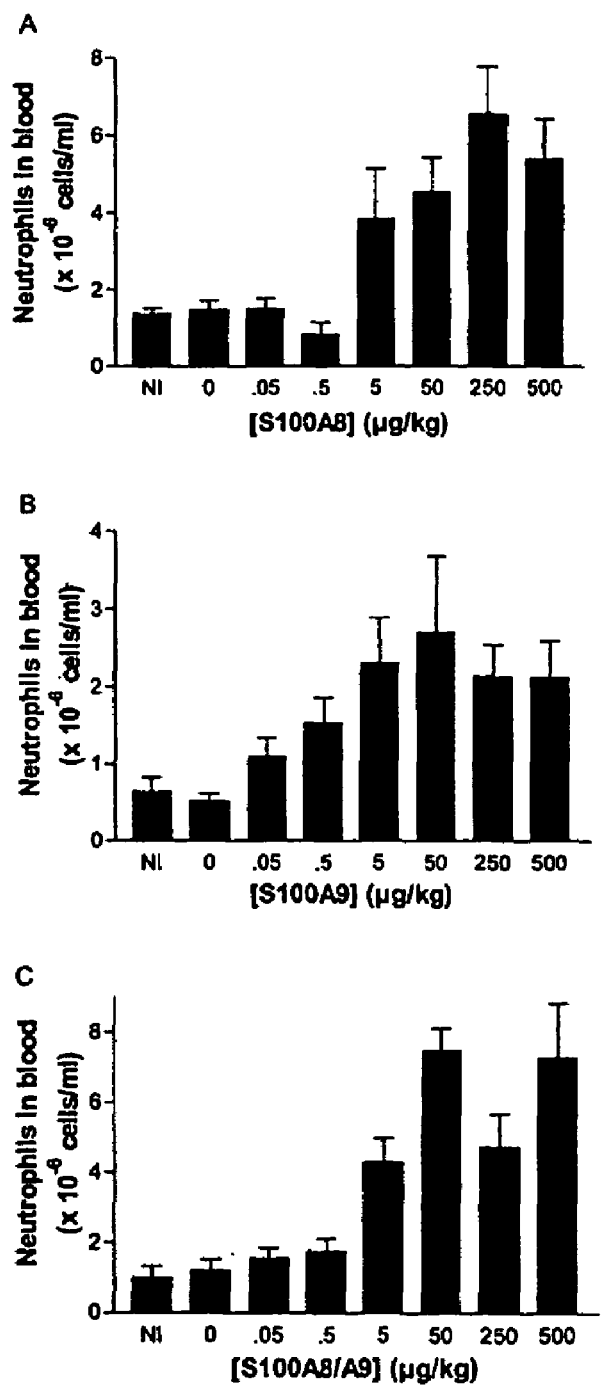
FIGS. 10A to 10C illustrate the accumulation of neutrophils in blood after i.v. injection of S100A8, S100A9, and S100A8/A9.

Intravenous Injection of S100A8, S100A9, and S100A8/A9 Results in Neutrophilia in Mice The fact that the levels of S100A9 and S100A8/A9 correlated with the LPS-induced neutrophilia suggested that these proteins could participate in the neutrophilia associated with injection of LPS. The anti-S100A8 and anti-S100A9 could therefore inhibit neutrophil migration indirectly, following a reduction of the circulating neutrophil caused by an inhibition of LPS-induced neutrophilia. To test this possibility, increasing doses of S100A8, S100A9, and S100A8/A9 were injected i.v. in mice and the peripheral blood was collected 3 hours later. As shown in FIGS. 10A, B and C, i.v. injection of S100A8, S100A9, and S100A8/A9 caused an increase in the number of circulating neutrophils. The number of neutrophils after injection reached 6.5, 2.7 and 7.4×10$^6$ cells/ml in S100A8, S100A9, and S100A8/A9 injected mice respectively, compared to less than 1.5×10$^6$ cells/ml for the control animals. This increase, detected for injected doses ranging from 5 to 500 µg/kg (0.12 to 12 µg/mice), was significantly different from control (p<0.05, Dunnett multiple comparison test) and maximum at a dose of 50 to 250 µg/kg. Although the total number of circulating leukocytes increased slightly in S100 protein-injected mice, this increase was not significantly different from that in PBS-injected mice. Assuming a total blood content of 79 ml/kg, these doses corresponded to serum concentrations ranging approximately from 600 to 3000 ng/ml at the time of injection. These doses are similar to the ones measured following injection of LPS in the air pouch (FIGS. 6B-D).

S100A8, S100A9, and S100A8/A9 Induce the Release of Bone Marrow Neutrophils

Figure 11:
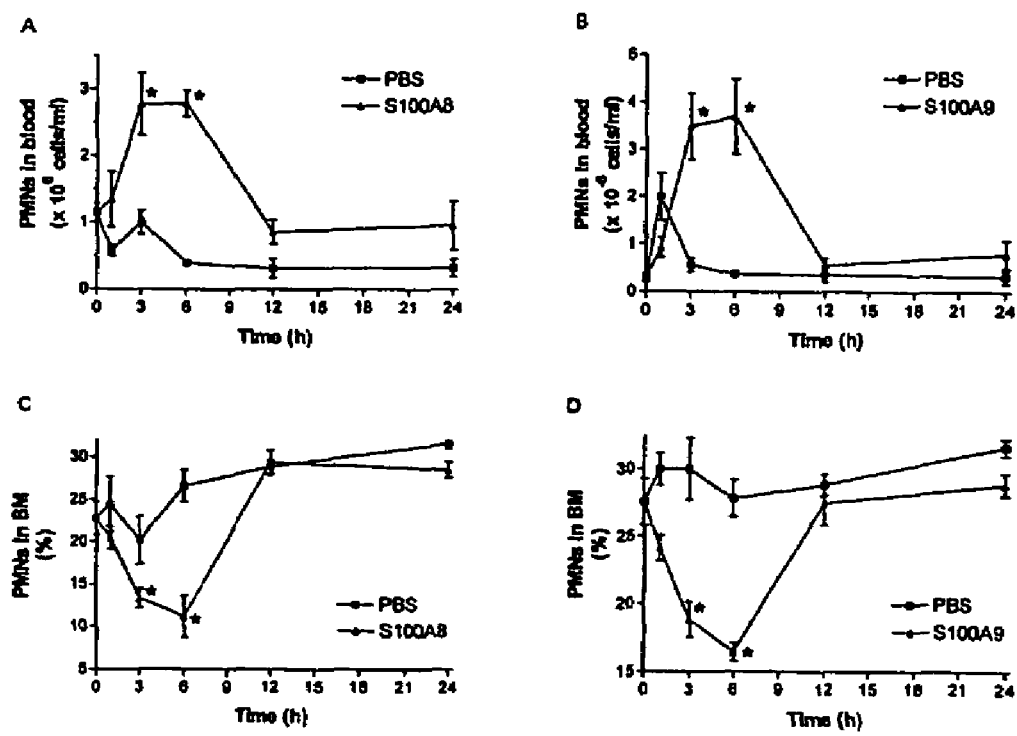
FIGS. 11A to 11D illustrate the mobilization of neutrophils from the bone marrow to the blood after injection of S100A8 and S100A9.

The kinetic study of S100A8 and S100A9 injection over a 24 h period (FIGS. 11A and B) showed that they induced neutrophilia over a period of 3 to 6 h post-injection. At 3 h, the number of neutrophils was 2.8×10$^6$±0.5×10$^6$ cells/ml in S100A8 -injected mice and 3.5×10$^6$±0.7×10$^6$ in S100A9-injected mice, compared to 1.0×10$^6$±0.2×10$^6$ cells/ml for the control mice (p<0.05, Bonferroni test). The increase in circulating neutrophils returned to the control levels by 12 h post-injection. The increase in the number of neutrophils in the blood induced by S100A8 and S100A9 closely correlated with a decrease in those of the bone marrow (FIGS. 11C and D). Approximately 22 to 27% of the bone marrow cells in non-injected mice were segmented and non-segmented neutrophils. This percentage did not vary significantly in PBS-injected mice. In contrast, the proportion of neutrophils decreased by 50% in bone marrow cells 3 and 6 h post injection of S100A8 or S100A9 (p<0.01 and p<0.05, respectively). This strongly suggest that S100A8 and S100A9 induce the release of neutrophils from the bone marrow to the blood.

Figure 12:
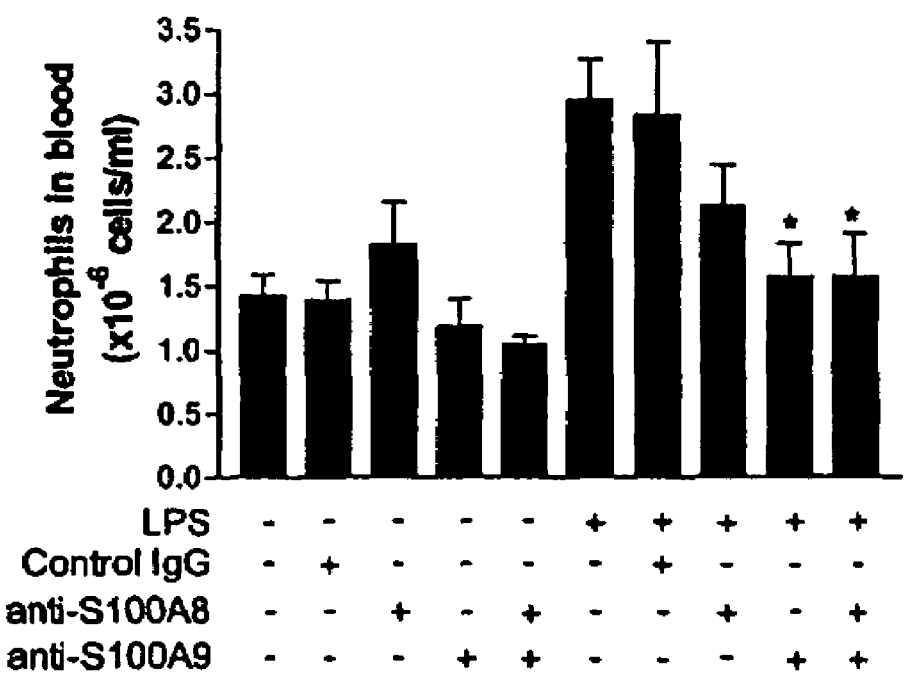
FIG. 12 illustrates the effect of anti-S100A8 and anti-S100A9 on LPS-induced neutrophilia.

Anti-S100A8 and Anti-S100A9 Inhibit the Neutrophilia Induced by Injection of LPS in the Air Pouch To evaluate the role played by S100A8 and S100A9 in LPS-induced neutrophilia, mice were injected i.p. with purified rabbit IgG against S100A8 and S100A9. LPS was then injected in the air pouches and the number of circulating neutrophils was measured 3 h later. As shown in FIG. 12, injection of anti-S100A9 led to an almost complete inhibition of the neutrophilia associated with the local injection of LPS (p<0.05 Bonferroni test). This inhibition was not increased when anti-S100A8 and anti-S100A9 were injected together. Although the anti-S100A8 also diminished the neutrophilia associated with LPS injection, this inhibition was not significant. As expected, the anti-S100A8, anti-S100A9, and the control IgG had no effect on the number of circulating neutrophils in PBS-injected mice.

Discussion

In the present experiment, it was demonstrated that S100A8, S100A9, and S100A8/A9 are released in the air pouch exudates and serum during an inflammatory reaction induced by LPS. Their presence in the exudates preceded the migration of neutrophil to the air pouch, while S100A9 and S100A8/A9 presence in serum correlated with LPS-induced neutrophilia. S100A8, S100A9, and S100A8/A9 induced the release of neutrophils from the bone marrow to the blood when injected i.v. and neutrophil accumulation when injected in the air pouch. Finally, passive immunization with purified IgG against S100A8 and S100A9 resulted in the inhibition of neutrophilia and neutrophil migration to the air pouch.

The kinetic of neutrophil accumulation to the air pouch offers a way of deciphering the role of S100A8 and S100A9 in the sequential steps of the mechanism of neutrophil migration from the bone marrow to the inflammatory site. Preliminary results using intravital microscopy demonstrated that neutrophil emigration from the blood vessel to the air pouch tissue begins within the first hour following injection of LPS and that neutrophils do not reach the air pouch lumen before 2 h post-injection. Consequently, exudates neutrophils at 3 h post-injection emigrated from the blood at the most 1 h post-injection. As shown in FIG. 8, the number of circulating neutrophils is not increased at 1 h post-injection. This indicates that exudates neutrophils at 3 h post-injection originate mostly from the pre-injection peripheral blood pool of neutrophils. Blocking molecules at the 3 h time point therefore provide indications about the role of the blocked molecule in neutrophil migration from the blood to the inflammatory site. In contrast, by 6 h post-injection, neutrophils had enough time to be released from the bone marrow storage pool, circulate in the peripheral blood and emigrate to the exudates. As a consequence, inhibition by blocking antibodies at 6 h post-injection can be due to the inhibition of neutrophil release from the bone marrow or neutrophil migration to the inflammatory site. These two possibilities can be further resolved by analysing the effect of the blocking antibodies on the numbers of circulating blood neutrophils at 3 h post-injection of LPS.

By analysing the effect of the blocking Abs at the two time points, it can be concluded that S100A8 and S100A9 play a role at the levels of both neutrophil migration to the air pouch and neutrophil release from the bone marrow respectively. Proofs of this comes from the fact that anti-S100A8 inhibited neutrophil migration to the air pouch at 3 h post-injection of LPS (FIG. 7A), but failed to significantly reduce neutrophil release from the bone marrow (FIG. 12). In addition, by 3 h post-injection, 2.1×10$^6$ neutrophils had migrated to the air pouch, which is less than the approximately 3×10$^6$ neutrophils circulating in the blood of a resting mouse. This indicates that by 3 h post-injection, the pouch neutrophils originated from the circulating, but not the bone marrow storage pool of neutrophils. Since no increase in peripheral blood neutrophils was detected in LPS-injected mice before 3 h post-injection, this suggests that the anti-S100A8 IgG directly inhibited neutrophil migration to the air pouch. Therefore, the role of S100A8 would be to assist in neutrophil migration to the inflammatory site. Support for this hypothesis comes from the fact that murine S100A8 was found to be chemotactic for neutrophils, and to activate Mac-1, an integrin important in neutrophil transendothelial migration.

At 6 h post-injection of LPS, the combination of anti-S100A8 and anti-S100A9 inhibited neutrophil migration to the air pouch (FIG. 7B).

It is contemplated that the polypeptides, compositions and methods of the present invention may also be useful in veterinary applications, as well as in the treatment of humans.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for the treatment of gout in a human suffering therefrom, comprising administering to said human a therapeutically effective amount of an antibody directed against S100A8 protein in combination with an antibody directed against S100A9 protein, wherein said therapeutically effective amount is sufficient to inhibit the migration of neutrophils involved in the pathogenesis of gout.

2. The method of claim 1, wherein said administration is selected from the group consisting of: intravenous, oral, intranasal, subcutaneous, topical and intraperitoneal administration.

* * * * *